(12) United States Patent
Goldenberg et al.

(10) Patent No.: US 10,064,608 B2
(45) Date of Patent: Sep. 4, 2018

(54) BIOPSY NEEDLE

(71) Applicants: Alec Goldenberg, New York, NY (US); Paul Hendrixson, Cumming, GA (US); Paul Gianneschi, Atlanta, GA (US)

(72) Inventors: Alec Goldenberg, New York, NY (US); Paul Hendrixson, Cumming, GA (US); Paul Gianneschi, Atlanta, GA (US)

(\*) Notice: Subject to any disclaimer, the term of this patent is extended or adjusted under 35 U.S.C. 154(b) by 335 days.

(21) Appl. No.: 14/939,805

(22) Filed: Nov. 12, 2015

(65) Prior Publication Data

US 2016/0135794 A1 May 19, 2016

Related U.S. Application Data

(60) Provisional application No. 62/081,257, filed on Nov. 18, 2014, provisional application No. 62/170,934, filed on Jun. 4, 2015.

(51) Int. Cl.
*A61B 10/02* (2006.01)

(52) U.S. Cl.
CPC ...... *A61B 10/0275* (2013.01); *A61B 10/0233* (2013.01); *A61B 10/0266* (2013.01); *A61B 2010/0208* (2013.01)

(58) Field of Classification Search
CPC ........ A61B 2010/0208; A61B 10/0233; A61B 10/0266–10/0275
See application file for complete search history.

(56) References Cited

U.S. PATENT DOCUMENTS

| | | | |
|---|---|---|---|
| 4,699,154 A | 10/1987 | Lindgren | |
| 4,958,625 A | 9/1990 | Bates et al. | |
| 5,843,001 A | 12/1998 | Goldenberg | |
| 6,015,391 A * | 1/2000 | Rishton | A61B 10/0266 600/562 |
| 6,033,369 A | 3/2000 | Goldenberg | |
| 6,340,351 B1 | 1/2002 | Goldenberg | |
| 7,207,950 B2 | 4/2007 | Goldenberg | |
| 7,226,423 B2 | 6/2007 | Goldenberg | |
| 7,278,970 B2 | 10/2007 | Goldenberg | |
| 7,338,456 B2 | 3/2008 | Goldenberg | |
| 7,384,400 B2 | 6/2008 | Goldenberg | |
| 7,455,645 B2 * | 11/2008 | Goldenberg | A61B 10/025 600/562 |
| 7,608,048 B2 | 10/2009 | Goldenberg | |
| 7,608,049 B2 | 10/2009 | Goldenberg | |

(Continued)

*Primary Examiner* — Michael C Stout
(74) *Attorney, Agent, or Firm* — Leason Ellis LLP

(57) ABSTRACT

A biopsy needle for collecting a tissue specimen includes an outer cannula that is at least partially received within a handle housing and an inner tube received within the outer cannula and configured to receive a stylet. A snare coil is attached between the inner tube and the outer cannula and a movable base is disposed within the handle housing. The outer cannula is fixedly coupled to the base and the movable base is axially movable within the handle housing. An inner driven structure that is coupled to the inner tube is configured to travel axially across an upper surface of the movable base. The coupling between the inner driven structure and the inner tube is such that the axial driving of the inner driven structure imparts rotation to the inner tube relative to the outer cannula.

20 Claims, 8 Drawing Sheets

(56) References Cited

U.S. PATENT DOCUMENTS

| | | |
|---|---|---|
| 7,621,923 B2 | 11/2009 | Goldenberg |
| 7,700,046 B2 | 4/2010 | Goldenberg |
| 7,731,667 B2 | 6/2010 | Goldenberg |
| 8,398,566 B2 | 3/2013 | Goldenberg |
| 8,500,654 B2 | 8/2013 | Goldenberg |
| 8,894,586 B2 | 11/2014 | Goldenberg |
| 9,211,113 B2 * | 12/2015 | Goldenberg |
| 2005/0054947 A1 * | 3/2005 | Goldenberg ....... A61B 10/0233 600/567 |
| 2007/0219460 A1 | 9/2007 | Goldenberg |
| 2008/0281223 A1 * | 11/2008 | Goldenberg ....... A61B 10/0266 600/567 |
| 2008/0281226 A1 | 11/2008 | Peters |
| 2009/0118641 A1 | 5/2009 | Van Dam et al. |
| 2009/0204023 A1 | 8/2009 | Goldenberg |
| 2009/0227895 A1 * | 9/2009 | Goldenberg ....... A61B 10/0266 600/567 |
| 2011/0004120 A1 | 1/2011 | Drubetsky |
| 2012/0150066 A1 * | 6/2012 | Goldenberg ....... A61B 10/0275 600/562 |
| 2015/0073299 A1 * | 3/2015 | Vetter ................ A61B 10/0266 600/564 |
| 2016/0135793 A1 | 5/2016 | Goldenberg |
| 2016/0135794 A1 | 5/2016 | Goldenberg |

* cited by examiner

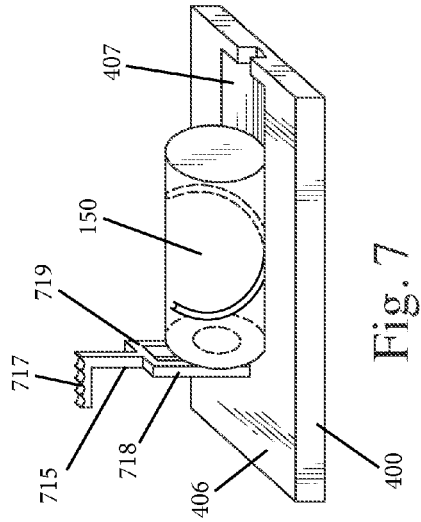
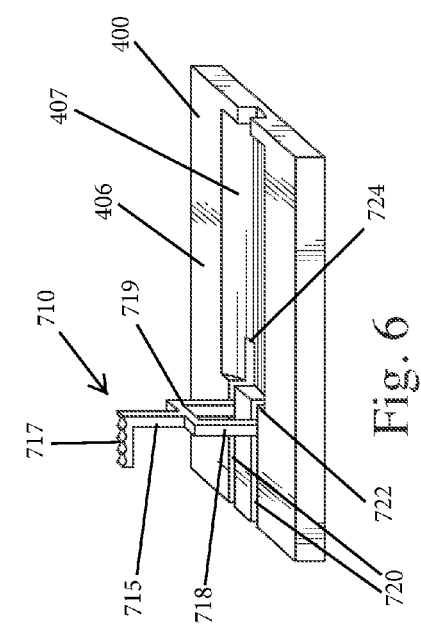
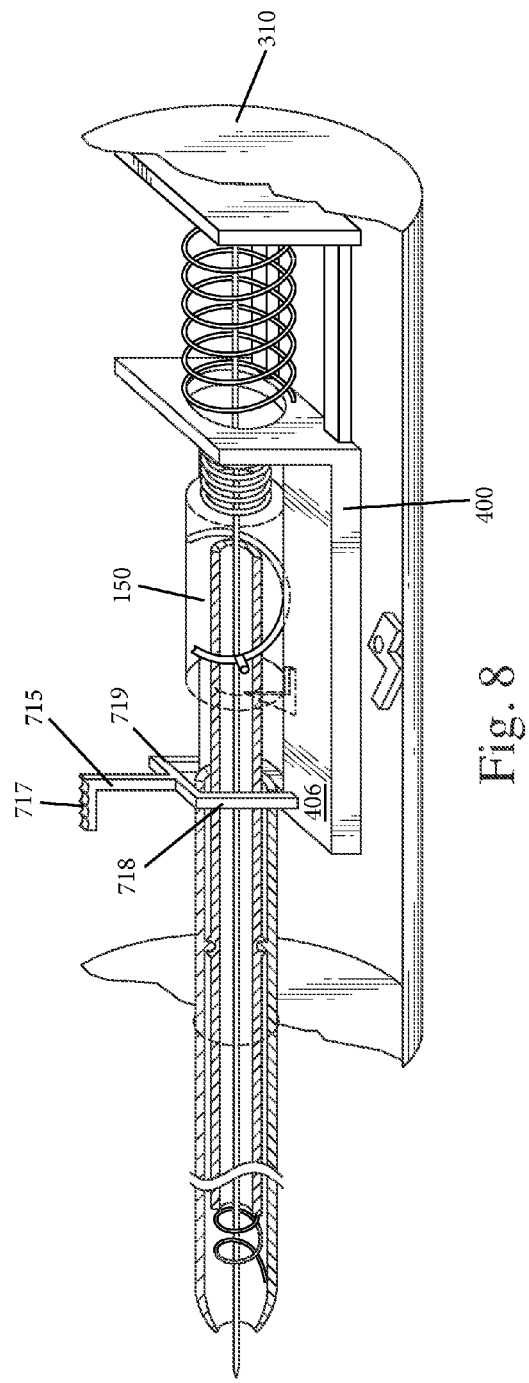

BIOPSY NEEDLE

CROSS-REFERENCE TO RELATED APPLICATIONS

This patent application is based on and claims priority to U.S. patent application Ser. No. 62/081,257, filed Nov. 18, 2014 and U.S. patent application Ser. No. 62/170,934, filed Jun. 4, 2015, each of which is hereby respectively incorporated by reference as if set forth in its respective entirety herein.

TECHNICAL FIELD

The present invention relates to a surgical instrument, typically known as a biopsy device used to obtain tissue samples of a target specimen and more particularly, relates to a minimally invasive biopsy device that allows an operator to more precisely obtain substantially larger tissue samples by manipulating the device's cutting mechanism for efficient engagement with a lesion or mass, resulting in improved sampling of organs or other anatomical structures.

BACKGROUND

Patients are undergoing more minimally invasive procedures as alternatives to open surgical procedures. These less invasive procedures use a variety of devices which are placed in organs and tissues, or abdominal, pulmonary, urologic spaces with the goal of manipulating, cutting, capturing and/or stabilizing structures at a distance from the operator. Retrieval of samples of tissues, masses, or lymph nodes may be required for histopathologic diagnosis. In addition operative procedures may require the removal of tissue components to achieve the requisite surgical result.

Standard or direct explorations or excisions of device components or retained materials, can be overly invasive and traumatic, and inconsistent with the basic principles of minimizing direct trauma through minimally invasive procedures. Therefore, minimally invasive devices and techniques have been developed to retrieve samples of suspicious lesions, masses or objects from the body. In addition standard direct explorations to excise tissue specimens can also be overly invasive and traumatic and are preferably completed with minimally invasive procedures.

There are a number of shortcomings in the designs of conventional biopsy devices and their application in clinical practice which limits their effectiveness and/or simplicity. The success of the biopsy procedure depends on the ability of the sampling device to efficiently and reliably obtain the foreign material. Similarly, the success of a biopsy procedure depends on the ability of the biopsy device to efficiently and reliably capture a portion of tissue. The initial steps of a biopsy procedure require that the sampling device must come in contact with the foreign material in a way that allows the device to engage it.

The object of the present invention is to provide a device that overcomes these deficiencies and improves the biopsy procedure.

Other features and advantages of the present invention will be apparent from the following detailed description when read in conjunction with the accompanying drawings.

SUMMARY

A biopsy needle for collecting a tissue specimen includes an outer cannula that is at least partially received within a handle housing and an inner tube received within the outer cannula and configured to receive a stylet. A snare coil is attached between the inner tube and the outer cannula and a movable base is disposed within the handle housing. The outer cannula is fixedly coupled to the base and the movable base is axially movable within the handle housing. An inner driven structure that is coupled to the inner tube is configured to travel axially across an upper surface of the movable base. The coupling between the inner driven structure and the inner tube is such that the axial driving of the inner driven structure imparts rotation to the inner tube relative to the outer cannula.

The needle includes a first biasing mechanism coupled to the movable base for driving the movable base in a distal direction when the first biasing mechanism releases its stored energy and a second biasing mechanism is coupled to the inner driven structure for driving the inner driven structure in a distal direction when the second biasing mechanism releases its stored energy. The first biasing mechanism defines a first stage of operation and the second biasing mechanism defines a second stage of operation. In the first stage, the release of the stored energy of the first biasing mechanism causes the movable base and the inner tube and the outer cannula to travel axially in the distal direction and the second biasing mechanism is configured such that after the movable base travels a prescribed distance. The second biasing mechanism releases its stored energy to cause rotation of the inner tube relative to the outer cannula, thereby causing activation of the snare coil.

DETAILED DESCRIPTION OF THE DRAWING FIGURES

FIG. 6 is side perspective view of a reset mechanism according to one embodiment;

FIG. 7 is a side perspective view of a reset mechanism according to another embodiment;

FIG. 8 is a side perspective view of a reset mechanism being shown in a first position.

DETAILED DESCRIPTION OF CERTAIN EMBODIMENTS

Figure 1:
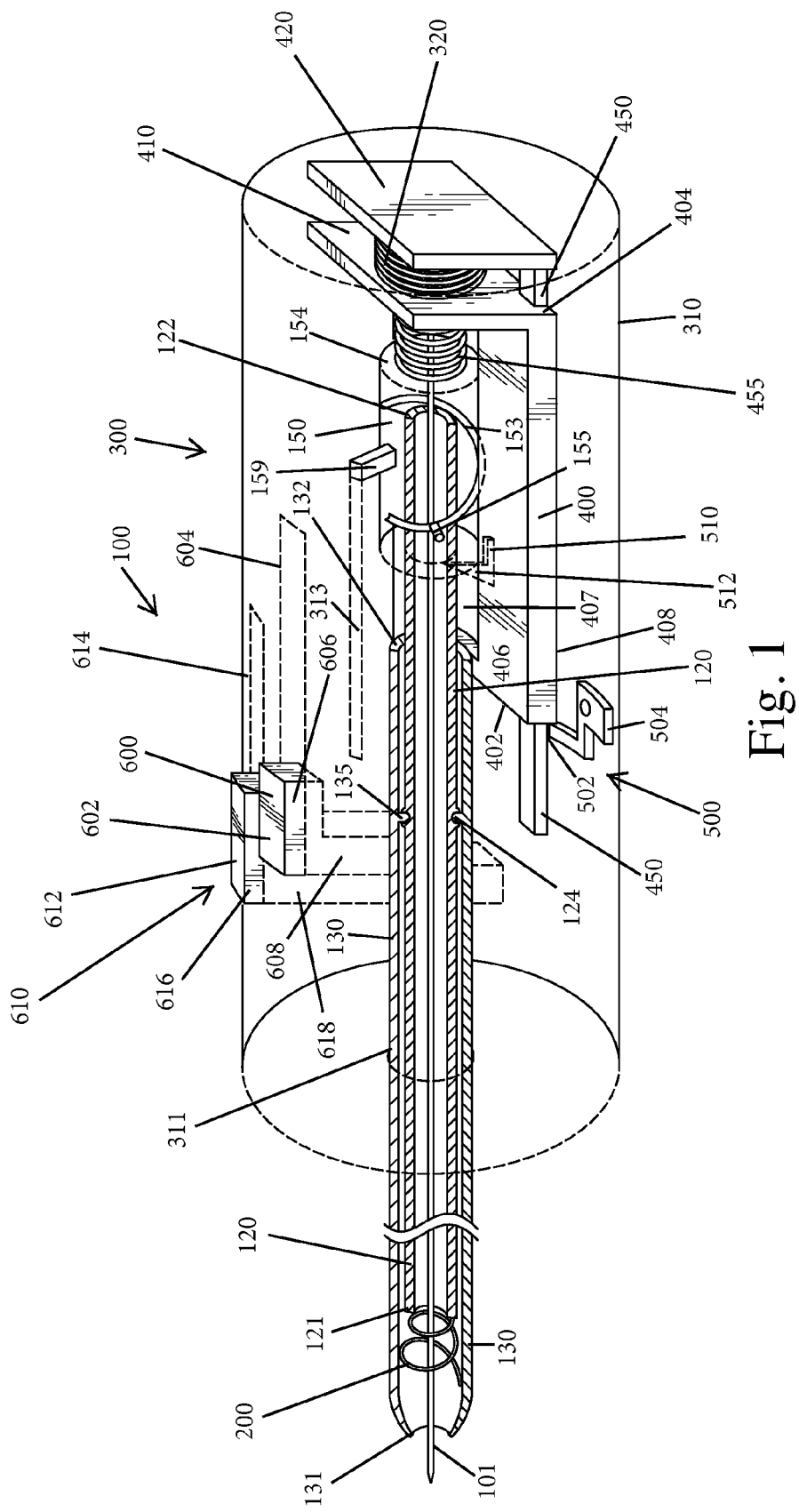
FIG. 1 is a side perspective view of a biopsy device in an initial position prior to actuation.
Figure 2:
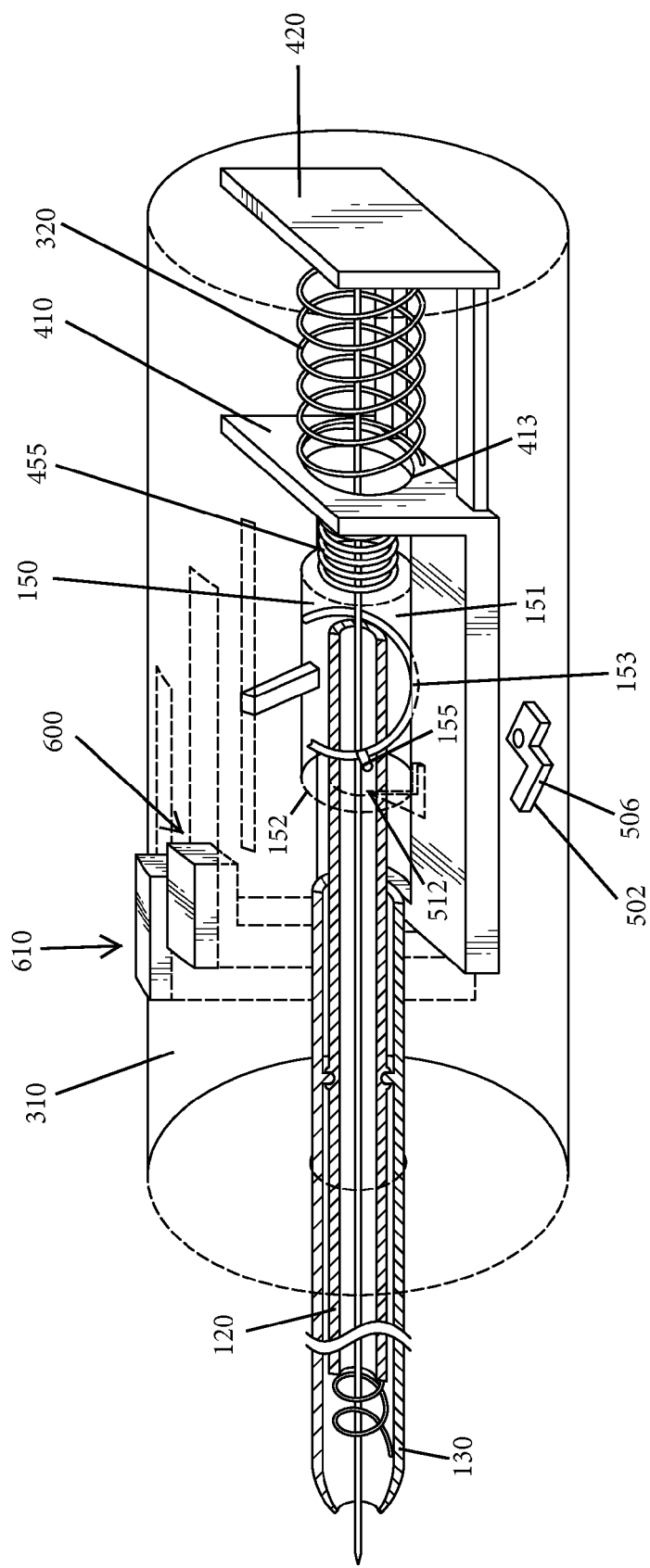
FIG. 2 is a side perspective view of the biopsy device after completion of a first stage of operation.
Figure 3:
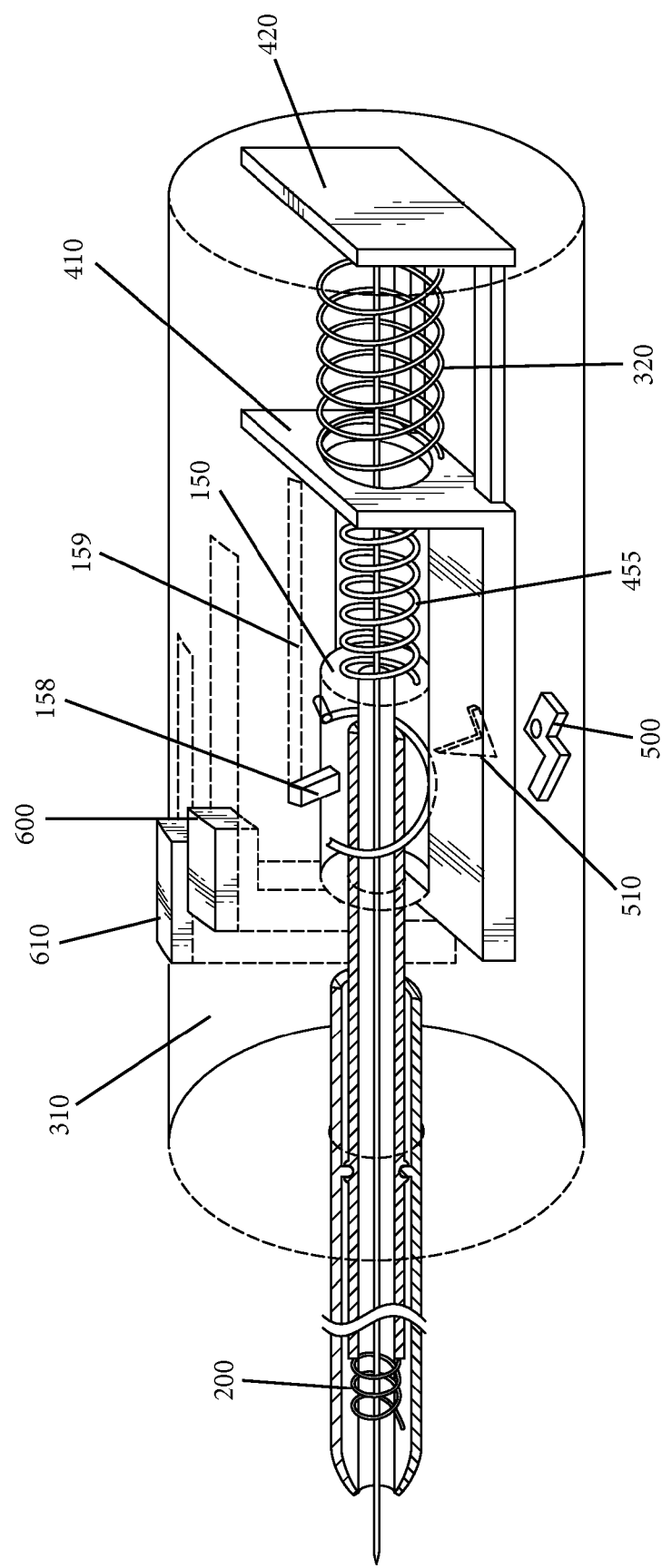
FIG. 3 is a side perspective view of the biopsy device after completion of a second stage of operation.

Now referring to FIGS. 1-3 in which a biopsy device 100 (specimen retrieving and capturing device or biopsy needle) of a snare coil design is illustrated and is configured to retrieve a target specimen which can be in the form of a tissue specimen or a foreign material that is located in certain organs or anatomical structures. To facilitate entry of the biopsy/capturing device 100 into organs or anatomical structures or duct channels, the device 100 incorporates a catheter system.

Referring now to FIGS. 1-3, the retrieval device (biopsy needle) 100 according to one exemplary embodiment is illustrated. The biopsy needle 100 includes an inner tube 120 with a wire 200 at a distal end thereof, an outer cannula 130, a stylet 101 and a handle assembly 300. In one aspect of the present invention, the handle assembly 300 includes a biasing (spring loaded) mechanism described in greater detail below that permits the user to selectively actuate the biopsy needle 100 so that the outer cannula 130 and the inner tube 120 are rapidly advanced beyond the stylet 101 to provide a shearing action of the soft tissue specimen.

The present biopsy needle 100 is particularly constructed for soft tissue biopsy applications since the spring loaded mechanism provides an improved means of removing the tissue after it is cored as well as providing an improvement in the way that the tissue is acquired by the biopsy needle 100. The handle assembly 300 includes a handle body 310 that can be formed in a number of different shapes and sizes and is generally a hollow body that contains the spring loaded mechanism. For purpose of illustration only, the handle body 310 of FIG. 1 is a generally rectangular or cylindrical or square body; however, handle body 310 preferably is an ergonomically pleasing shape that allows for secure grasping and accurate positioning of the needle tip by the operator.

The inner tube 120 includes a distal end 121 and an opposing proximal end 122. The inner tube 120 can have any number of different cross-sectional shapes; however, in one embodiment, the inner tube 120 has a circular cross-section. The inner tube 120 can include an annular shaped groove 124 that is spaced from the proximal end 122.

The outer cannula 130 can be similar or identical to the outer tube disclosed in one of the aforementioned patents. More specifically, the outer cannula 130 can include a distal end 131 and an opposing proximal end 132. The outer cannula 130 can also have any number of different cross-sectional shapes with one embodiment being a circular tube structure. At or near the proximal end of the outer cannula 130, the outer cannula 130 can include a protrusion 135, such as a bump, that mates with and is received within the annular groove 124. A snap-fit can be formed between the outer cannula 130 and the inner tube 120. The reception of the protrusion 135 into the annular groove 124 couples the two members together such that the two members move longitudinally in unison, while the inner tube 120 can rotate relative to the outer cannula 130 (i.e., the bump travels within the annular groove).

In accordance with the present invention, the inner tube 120 and the outer cannula 130 are coupled to one another such that the inner tube 120 and the outer cannula 130 move together, in unison, in an axial direction, while the inner tube 120 is permitted to rotate relative to the outer cannula 130 for activating and deactivating the snare. Any number of different mechanisms can be used to achieve the foregoing coupling between the outer cannula 130 and the inner tube 120.

Figure 1A:
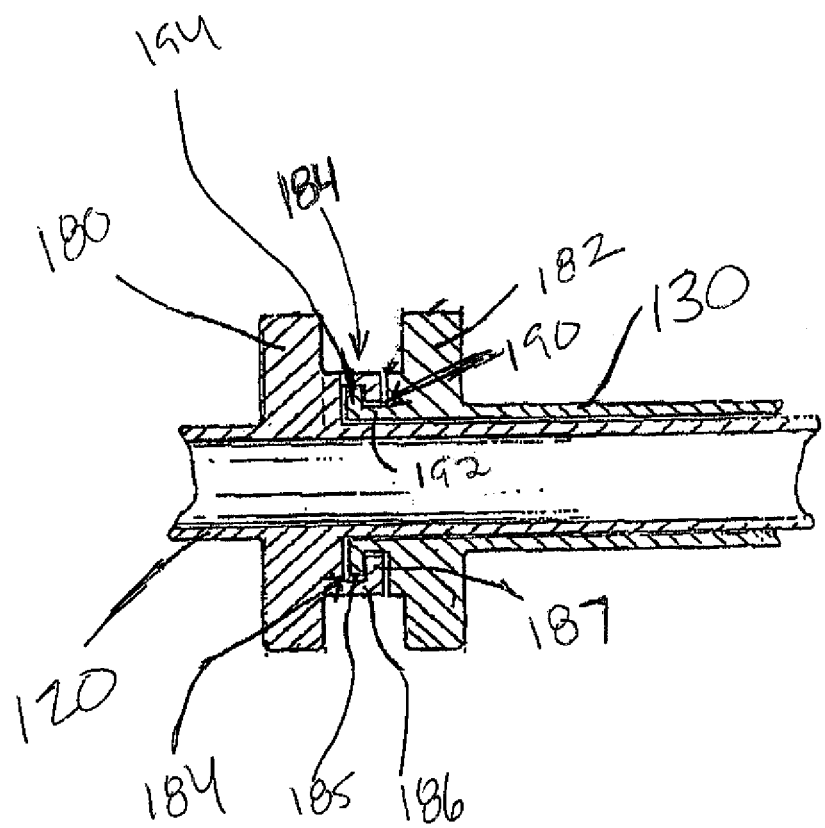
FIG. 1A is a cross-sectional view of an alternative mechanism for coupling an inner tube and outer cannula of the device.

Alternatively and as shown in FIG. 1A, the inner tube 120 can include a flange 180 that is spaced from the proximal end 122 and extends outwardly from the inner tube 120. The flange 180 can be in the form of an annular flange that extends completely around the inner tube 120 or it can be in the form of one or more protrusions, e.g., tabs, that extend outward from the inner tube 120. The flange 180 can be in the form of an annular ring.

Alternatively, at the proximal end 132 of the outer cannula 130, a flange 182 is formed. As with the flange 180 formed as part of the inner tube 120, the flange 182 of the outer cannula 130 can be in the form of an annular flange or it can be formed by one or more protrusions or tabs.

The inner tube flange 180 and the outer tube flange 182 can be positioned adjacent to each other along the longitudinal axis of the inner tube/outer tube assembly to limit displacement of the tubes relative to each other when they are both projected forward or repositioned back into the handle assembly. Alternatively, the inner tube flange 180 may be positioned adjacent to the proximal end of the outer tube 130 to limit displacement of the inner and outer tubes 120, 130 relative to each other during forward projection of the inner/outer tube or repositioning of the inner/outer tube into the handle assembly. In this side by side flange configuration, the inner and outer tubes 120, 130 remain aligned and move uniformly without displacing the one tube relative to the other tube, partly as a result of the lip and groove engagement mechanism represented by the annular groove 124 and the protrusion 135.

In one embodiment, shown in FIG. 1A, in which the inner tube 120 and outer cannula 130 include flanges 180, 182, respectively, the flange 180 of the inner tube 120 includes a first locking lip 184 that creates a space 185 between the lip 184 and the flange 180. The first locking lip 184 has a first portion 186 and a second portion 187 that is parallel to the flange 180, with the first portion 186 being perpendicular to the flange 180 and connects the second portion 187 to the flange 180.

The outer cannula 130 includes a complementary second locking lip 190 that is received within space 185 between the first locking lip 184 and the flange 180, thereby coupling the parts 120, 130 to one another. The second locking lip 190 has a first portion 192 and a second portion 194 that is parallel to the flange 182, with the first portion 192 being perpendicular to the flange 182 and connects the second portion 194 to the flange 182. The second portion 194 is parallel to flange 182. The second portion 194 is thus received within the space 185, thereby coupling the two 120, 130 together in a longitudinal direction, while permitting the two 120, 130 to rotate relative to one another. In this manner, the lip portions interlock with one another and prevent independent axial movement between the inner tube 120 and the outer cannula 130, while still permitting rotation of the inner tube 120 relative to the outer cannula 130.

In the case of the protrusion 135 and annular groove 124 embodiment, as illustrated, the protrusion 135 is received in the groove 124 and releasably retained therein.

The handle body 310 includes an opening 311 formed at a distal end thereof through which the combined inner tube 120/outer cannula 130 pass. The opening 311 allows the combined inner tube 120/outer cannula 130 to move in the axial direction between the retracted position and the extended position in which more of the combined inner tube 120/outer cannula 130 is exposed distally beyond and outside of the handle body 310. This opening 311 allows the combined inner tube/outer cannula to be fired and retracted as described herein.

Both the inner tube 120 and the outer cannula 130 are axially movable through the displacement of a movable base 400 that is disposed within the handle body 310. The movable base 400 can be thought of as being a sled that is controllably moved a defined distance within the hollow interior of the housing 300. The base 400 has a first end 402, an opposing second end 404, a top surface 406 and an opposing bottom surface 408. In accordance with the present invention, the combined inner tube 120/outer cannula 130 are coupled to the base 400 such that the axial movement of the base 400 (in either direction) is translated into axial movement of the combined inner tube 120/outer cannula 130. More specifically, the outer cannula 130 can be coupled to the top surface 406 of the base 400 using any suitable technique. For example, a mechanical coupling (fit) can be formed or an adhesive or chemical bonding can be used.

In one embodiment, the combined inner tube 120/outer cannula 130 is fixedly attached to the base 400 such that the base 400 acts as a carrier for the combined inner tube 120/outer cannula 130.

In one embodiment, the top surface 406 has a contoured surface in which the top surface 406 includes a recessed section and more specifically, the recessed section in the top surface 406 comprises a concave section 407 defined by a concave surface. The concave surface 407 does not have to extend the entire length of the top surface 406 but instead can only extend a length thereof less than the entire length. When the concave surface 407 does not extend to either of the ends of the base 400, the concave surface 407 can be defined by a first end edge and/or a second end edge. As described below, one or more of these end edges can act as a stop. Alternatively, the top surface recessed section may be configured in other non-concave morphologic conformations.

There are any number of different ways to construct the base 400 such that it is axially movable within the handle body 310. In particular, the base 400 can ride along one or more guides 450 that permit axial movement both in a distal direction and a proximal direction. For example, a pair of guides 450 can be provided with each of the guides 450 being in the form of an elongated rod. The two rods 450 are fixedly anchored at their ends to the ends of the handle body 310. The two rods 450 are thus spaced apart from one another and are parallel to one another. The base 400 has a pair of bores formed along a length thereof and configured to receive the rods 450. The base 400 thus freely rides along the rods 450 in both a distal axial direction and a proximal axial direction. The rods 450 also support and suspend the base 400 within the hollow interior of the handle body 310.

Alternatively, the base 400 can have one or more tabs or fingers that depress downwardly therefrom and are received within a complementary received track formed in the handle body 310. The recessed track is a longitudinal track that allows the base 400 to move in an axial direction within the handle body 310. The ends of the track define the ends of travel of the base 400.

The base 400 can have any number of different shapes including a rectangular or square shape as shown.

As shown, one end (e.g., the proximal end) of the base 400 includes a first support member or wall 410. The wall 410 is a vertical wall that extends upwardly from the base 400. The wall 410 can extend across the entire width of the base 400 as shown. The wall 410 can also include an opening 413 (FIG. 2), such as a circular opening as shown. The opening 413 can be configured to allow the stylet to pass therethrough.

Within the interior of the handle body 310, a second support member or wall 420 can be provided. The second support member 420 can be attached to the proximal end of the stylet so as to permit the stylet to move relative to the combined inner tube/outer cannula, to facilitate extending the stylet further into the targeted tissue prior to releasing the combined inner tube/outer cannula into the tissue. However, in practice when activated, the needle projects the combined inner tube/outer cannula over the steadfast stylet. As understood, the stylet is used to initially locate and target the tissue to be biopsied in that the distal end of the stylet is placed into intimate contact with the target tissue.

The second support wall 420 is preferably parallel to the first wall 410. The second support wall 420 is oriented proximal to the first wall 410. The second support wall 420 can engage a lock mechanism that ensures that the second support wall 420 remains in a locked position. For example, a latch mechanism or the like can be used to lock the second support wall 420 in place. The handle body 310 can be constructed such that the second support wall 420 can be removed from the handle body 310 as by being removed through an opening formed in the handle body 310. Once the combined inner tube 120/outer cannula 130 project forward as described herein, the stylet can be removed to then allow removal of the captured tissue. Alternatively, the stylet remains in place and functions as a extracting dowel member which forces the tissue specimen from the internal aspect of the inner tube as the combined inner tube/outer cannula assembly is displaced back into the handle assembly for reactivation.

Before proceeding to an explanation of the other operable components of the spring loaded mechanism, it is helpful to understand that generally the inner tube 120 and outer cannula 130 are positionable between two positions, namely, a fully retracted position and a fully extended position. In the fully retracted position, the inner tube 120 and outer cannula 130 are reset back into the handle body 310 and a biasing element(s) of the spring loaded mechanism stores energy. In contrast, after the user activates the spring loaded mechanism, the biasing element releases its energy and an axial force is applied to the inner and outer tube structure in a direction away from the handle body 310, forcing the inner and outer tube structure into the tissue to be sampled.

In both the fully retracted and fully extended positions, the protrusion 135 is mated to the groove 124 coupled to one another, as described below, so that a force applied to one of the inner tube 120 and the outer cannula 130 is translated to the other of the inner tube 120 and outer cannula 130.

In order to generate a force that is sufficient to shear the soft tissue, the spring loaded mechanism includes a first biasing element 320, such as a coil spring, that applies a force against a face of the first wall 410. The size and/or location of the first biasing element 320 is selected such that the first biasing element 320 has a greater diameter than the opening 311, therefore lying outside the opening.

The first biasing element 320 is disposed between the first wall 410 and the second wall 420. The second wall 420 can be fixed in place such that the first biasing element 320 can be compressed between the two walls 410, 420 by moving the base 400 in a direction towards the second wall 420 since the base 400 is axially movable. The first biasing element 320 thus represents the means for axially projecting the combined inner tube 120/outer cannula 130.

The first biasing element 320 can be in the form of a spring (e.g., coil spring) that can store energy as well as other energy storing element(s). When the first biasing element 320 releases its energy, the spring exerts a force against the second support wall 420 to cause the axial movement of the entire base 400 in a distal direction since the second support wall 420 is attached to the base 400.

The device 100 also includes a means for causing the selective rotation of the inner tube 120 relative to the outer cannula 130. In particular, the means is in the form of a curvilinear tube 150 (which can be thought of as an inner driven structure). The curvilinear tube 150 has a first end 152 and an opposing second end 154. The curvilinear tube 150 is sized and configured to seat along the upper surface 406 of the base 400 and more particularly, the curvilinear tube 150 is disposed within the concave surface 407 of the upper surface 406 of the base 400. As described herein, the curvilinear tube 150 is axially movable within the concave surface 407 of the base 400. While the inner surface of the curvilinear tube is generally cylindrical, the outer surface need not be cylindrical and can take one of many shapes, even cubelike in nature, as long as the tube can be displaced axially along the surface 406 within a complementary shaped indentation.

The curvilinear tube 150 is coupled to the inner tube 120 such that the controlled axial displacement of the curvilinear tube 150 is translated into the controlled rotation of the inner tube 120, thereby providing the means for closing and opening the snare. The ends 152, 154 of the curvilinear tube 150 are open to allow passage of the stylet through the tube 150. In addition, the central opening of the curvilinear tube 150 allows for reception of the inner tube 120. The inner tube 120 can pass through the open first end 152 but not pass through the open second end 154 (in other words, the proximal end of the inner tube 120 is located internally within the interior of the tube 150).

The curvilinear tube 150 has an outer surface 151 and an inner surface. In one embodiment, a pin and groove mechanism is used to couple the inner tube 120 to the curvilinear tube 150. For example, the curvilinear tube 150 can include at least one groove 153 formed in the inner surface, with the groove 153 having a helical shape. It will be understood that the groove 153 can be in the form of a helical slot formed through the tube. The inner tube 120 includes at least one complementary pin 155 that is configured to be received within the groove 153. In one embodiment, the inner tube 120 can have a single pin 155 or the inner tube 120 can have a pair of pins 155 that are disposed opposite one another (180 degrees apart). When the inner tube 120 has a pair of pins 155, the curvilinear tube 150 has a pair of complementary slots/grooves 153 that are symmetrically opposite one another.

Each pin 155 extends radially outward from an outer surface of the inner tube 120. The pin 155 does not extend internally within the interior of the inner tube 120. In the case of having two pins 155, the pins 155 are axially aligned and extend radially outward from the outer surface of the inner tube 120 at two opposite points thereof.

Each pin 155 is received into the respective groove/slot 153 and the linear (axial) movement of the curvilinear tube 150 is translated into the pin 155 riding along the groove 153. Since the groove 153 has a helical shape, the pin 155 riding within the groove 153 causes rotation of the inner tube 120 since the curvilinear tube 150 is prevented from rotating within the handle body 310.

In yet another embodiment, the pin 155 can be associated with the curvilinear tube 150 (i.e., can protrude inwardly from the inner surface thereof) and the helical shaped groove 153 can be formed along the outer surface of the inner tube 120. As in the other embodiments, the pin 155 is received within the groove 153 and the firing of the curvilinear tube 150 causes the pin 155 to ride within and along the length of the groove 153. As in the previous embodiment, there can be more than one pin 155 and more than one corresponding groove 153 to create the desired rotation of the inner tube 120.

Any number of different mechanisms can be employed that permit the curvilinear tube 150 to move axially along the upper surface 406 of the base 400; however, the curvilinear tube 150 is prevented from rotating. Since the curvilinear tube 150 can only move in a linear direction, the inner tube 120 is the member that has rotation imparted thereto. In one embodiment, the outer surface of the curvilinear tube 150 can have a protrusion 159 extending radially outward therefrom, with the protrusion being received within a linear guide track or slot 313 313 formed in the handle body 310 (e.g., formed along a side wall of the body 310) or in the upper surface 406 of 400 or in the complimentary recess 407. The reception of the protrusion 159 within the linear track restricts the degree of motion of the tube 150 and in particular, forces the curvilinear tube 150 to only move in a linear direction along the upper surface 406 within the concave portion 407 and across the upper surface 406. In another embodiment, the protrusion 159 extending outward from the curvilinear tube 150 can be received within a linear guide slot formed in the base 400 and more particularly, formed within the concave portion 407 of the base 400. Both of these arrangements constrain the type of movement of the curvilinear tube 150 that is permissible and in particular, only allows the curvilinear tube 150 to be fired forward (linearly) and similarly retracted backwards (linearly) without it rotating around the longitudinal axis.

The device 100 also includes a second biasing mechanism 455 which serves to controllably fire the curvilinear tube 150 as part of a second stage of operation of the device. As described in detail herein, the second stage is operable after the first stage concludes. The first stage being again the forward advancement of the base 400 and the combined inner tube/outer cannula so as to drive the combined inner tube/outer cannula into the target tissue. The second biasing mechanism 455 is disposed between the proximal end of the curvilinear tube 150 and a distal face of the first wall 410. The second biasing mechanism 455 can be in the form of a spring or other elements that can reversibly store energy. Energy is stored when the spring 455 is compressed by reducing the distance between the proximal end of the curvilinear tube 150 and the first wall 410. As with the first biasing mechanism, the second biasing mechanism is positioned such that its diameter or outer aspect lies outside of the opening formed in the first wall 410 (to allow passage of the stylet).

In the initial position (loaded position) of the curvilinear tube 150, the spring 455 is compressed and stores energy. In the initial position, the curvilinear tube 150 is disposed proximally in the concave section 407 of the base 400. Under select conditions, when the second spring 455 releases its energy, the curvilinear tube 450 is propelled forward in a linear manner within the concave surface 407. The curvilinear tube 450 travels a prescribed distance that is sufficient to cause the pin(s) 155 to travel within the helical groove(s) 153 resulting in rotation being imparted to the inner tube 120 since the curvilinear tube 150 can only move linearly and axially. The pin 155 can travel the length of the groove or can travel a substantial length of the groove so long as the distance traveled is sufficient to cause the inner tube 120 to rotate sufficiently to cause activation of the snare.

The device 100 also includes a means for controllably firing both the base 400 and the curvilinear tube 150. More specifically, a first release (lock) member 500 is provided and is accessible to the user to cause the base 400 to be fired forward as a result of the release of the stored energy of the first biasing mechanism 320. The first release member 500 can take any number of different forms so long as it has a portion that is accessible to the user and has a portion that selectively engages the base 400. For example, the first release member 500 can be in physical engagement with the base 400 such that when the first release member 500 disengages the base 400, the stored energy of the first spring 320 is released. This results in the forward firing of the base 400 and also the combined inner tube/outer cannula. The first release member 500 can be in the form of a physical structure that locks the base 400 in the initial retracted position and when the physical structure is moved such that contact with the base 400 is eliminated, the base 400 is free to move linearly and the first spring 320 provides the energy to drive the base 400. In the illustrated embodiment, the first release member 500 is in the form of a movable catch 502 (claw) that engages a portion of the base 400. For example, the first release member 500 includes a first section 504 that lies outside of the handle body 310 and is accessible by the user. This first section 504 can be in the form of a button, a slider, etc. The first release member 500 has a second section 506 that is connected to the first section 504 (or is integral therewith) and represents the portion of the release member 500 that selectively engages the base 400. The second section 506 is movable, such as being pivotable, so as to allow the second section 506 and the 502 claw engaging section to be moved out of contact with the base 400 when the user manipulates the first section 504. The first release member 500 can be biased (as by a spring) such that it normally assumes one position. As described herein, a cam can be provided to facilitate the relocking of the base 400 after the two stages of operation are complete.

A second release (lock) member 510 is in the form of a physical structure that locks the curvilinear tube 150 in place along the base 400 in the initial retracted position and when the physical structure is moved such that contact with the curvilinear tube 150 is eliminated, the curvilinear tube 150 is free to move linearly and the second spring 450 provides the energy to drive the curvilinear tube 150 along the upper surface 406 of the base 400. In the illustrated embodiment, the second release member 510 is in the form of a movable catch 512 (claw or prong) that engages a portion of the curvilinear tube 150 (e.g., a front edge of the curvilinear tube).

Unlike the first release member 500, the second release member 510 is completely disposed internally within the handle body 310 and is not accessible by the user. As a result, the disengagement of the second release member 510 occurs automatically without user intervention when the base 400 reaches a certain location within the handle body 310. The second release member 510 is thus coupled to the base 400, and may be an integral part of the base 400. The second release member 510 is naturally biased in an upward position such that when the proper registration exists between the second release member 510 and the curvilinear tube 150, the second release member 510 actively engages the curvilinear tube 150 and prevents linear (longitudinal) movement thereof.

The catch 512 extends upward, possibly through an opening or slot formed in the base 400 to engage the distal end of the curvilinear tube 150. Alternatively, the curvilinear tube 150 can have a recess in which the catch 512 is received when the curvilinear tube 150 is in the retracted position and registration exists between tube 150 and the second release member 510. In the initial position of the base 400, the curvilinear tube 150 is also in the initial retracted position and the catch 512 is in engagement (intimate contact) with the distal end of the curvilinear tube 150. As the base 400 is projected (driven) forward by the release of the energy of the first spring 320, the catch 512 engages a cam surface that is located at a fixed location. When the catch 512 engages the cam surface, the catch 512 disengages from being in contact with the distal end of the curvilinear tube 150 (or disengages from a slot or recess formed in the tube 150), thereby releasing the curvilinear tube 150 and allowing the firing thereof (due to release of the stored energy of the second spring).

The base 400 is thus constructed to allow for the inclusion and operation of the second release member 510 in that during the firing of the base 400 in the first stage, the second release member 510 does not interfere with such movement of the base 400. Only when the base 400 has traveled a prescribed distance does the second release member 510 disengage from the curvilinear tube 150 resulting in the beginning of the second stage of operation.

Thus and in accordance with the present invention, the second release member 510 is not disengaged from the curvilinear tube 150 until the first stage reaches its completion or reaches its substantial completion. In other words, the curvilinear tube 150 is not advanced axially (fired forward) until the base 400 reaches its end of travel or reaches its substantial end of travel. This results in the second stage being activated after the first stage has been activated and has reached completion and consequently, the snare is only activated after the inner tube/outer cannula has been advanced into contact with the target tissue, and substantially penetrated the tissue.

The device 100 also preferably incorporates one or more stops for limiting the degree of travel of the base 400 and/or the curvilinear tube 150. For example, a first stop can be provided for stopping the base 400 and thus, terminate the forward progression (forward firing) of the base 400. The stop can be a tab or other protrusion that is located along the travel of the base 400. The stop can be located prior to the distal end of the handle body 310 so as to prevent the distal end of the base 400 from contacting the distal end (wall) of the handle body 310. A second stop is configured to limit the degree of travel of the curvilinear tube 150 along the upper surface 406 of the base 400. The second stop can take any number of different constructions including the concave section 407, which can terminate in a hard distal end edge that can act as a stop in that when the curvilinear tube 150 contacts this end edge, the axial travel of the curvilinear tube 150 ends. The second stop can alternatively be in the form of a protrusion that is located within the concave section 407. This protrusion serves to contact the end edge of the curvilinear tube 150 and prevent further axial movement in the distal direction. Yet another stop can be the end of the groove 153 formed in the curvilinear tube 150 in that when the pin 155 reaches the proximal end of the groove 153, the curvilinear tube 150 has reached its end of distal travel.

Each of these stops is designed to stop the respective movement of one of the base 400 and the curvilinear tube 150.

The device 100 can have one or more reset mechanisms that are used after the device 100 has competed both the first stage (firing of the inner tube/outer cannula into the target tissue) and the second stage (rotation of the inner tube relative to the outer cannula to cause activation of the snare). These may serve as stops for the base 400 and curvilinear tube 150, as well. In the embodiment shown in FIGS. 1-3, there are two separate reset mechanisms, namely, a first reset mechanism 600 for resetting the curvilinear tube 150 to its initial position and a second reset mechanism 610 for resetting the base 400 to its initial position.

The first reset mechanism 600 is configured to physically move the curvilinear tube 150 in the proximal direction and across the top surface 406 to the initial position. The first reset mechanism 600 can thus be a physical structure that contacts and applies a force against the curvilinear tube 150 (e.g., against the distal end thereof) and drive the curvilinear tube 150 to the initial position. However, the first reset mechanism 600 does not limit the distal projection of the base 400 or the curvilinear tube 150 and therefore does not interfere with the operation of both the base 400 and the curvilinear tube 150 (i.e., the forward firing of the base and combined inner tube/outer cannula).

The illustrated first reset mechanism 600 can be in the form of a slider 602 that travels within a guide slot 604 (linear slot) formed in the handle body 310. The slider 602 has a first section 606 that can be accessed by the user to allow the user to drive the slider 602 within the guide slot 604 and a second section 608 that extends downward from the first section 606. The second section 608 is the section that contacts and drives the distal end of the curvilinear tube 150 in the proximal direction to its reset position. The slider 602 can thus have an L shape as well as a variety of other configurations.

In one embodiment, the guide slot 604 has a length such that when the slider 602 is at a distal end thereof, the slider 602 is beyond the distalmost point of travel of the curvilinear tube 150. As a result, the slider 602 does not impede the travel (firing) of the curvilinear tube 150.

The slider 602 works by physically driving the curvilinear tube 150 in a proximal direction until the second release member 510 reengages with the curvilinear tube 150. The user can receive auditory feedback (a click noise) and/or tactile feedback (feel a clicking engagement) to indicate that the curvilinear tube 150 has been successfully reset. Once this confirmation (feedback) is received by the user, the user can then move the slider 602 in the distal direction toward a rest position thereof (which does not obstruct the subsequent firing of the curvilinear tube 150).

Similarly, the second reset mechanism 610 is configured to physically move the base 400 in the proximal direction. The second reset mechanism 610 can thus be a physical structure that contacts and applies a force against the base 400 (e.g., against the distal end thereof) and drive the base 400 to the initial position. However, the second reset mechanism 610 does not interfere with the operation of both the base 400 and the curvilinear tube 150 (i.e., the forward firing of the base and combined inner tube/outer cannula).

The illustrated second reset mechanism 610 can be in the form of a slider 612 that travels within a guide slot 614 (linear slot) formed in the handle body 310. The slider 612 has a first section 616 that can be accessed by the user to allow the user to drive the slider 612 within the guide slot 614 and a second section 618 that extends downward from the first section 616. The second section 618 is the section that contacts and drives the distal end of the base 400 in the proximal direction to its reset position. The slider 612 can thus have an L shape as well as other configurations. The locations of the two reset mechanisms 600, 610 are mutually coexistive in that the two sliders are radially offset from one another.

In one embodiment, the guide slot 614 has a length such that when the slider 612 is at a distal end thereof, the slider 612 is beyond the distalmost point of travel of the base 400. As a result, the slider 612 does not impede the travel (firing) of the base 400.

The slider 612 works by physically driving the base 400 in a proximal direction until the first release member 500 reengages with the base 400. The user can receive auditory feedback (a click noise) and/or tactile feedback (feel a clicking engagement) to indicate that the base 400 has been successfully reset. Once this confirmation (feedback) is received by the user, the user can then move the slider 612 in the distal direction toward a rest position thereof (which does not obstruct the subsequent firing of the base 400).

The operation of the device 100 is as follows. The device 100 is initially in a rest (retracted) position shown in FIG. 1. The user grasps the device 100 by the handle body 310 and then the user advances and/or places the stylet at the target tissue. The user then actuates the device by pressing, sliding or otherwise manipulating the first release member 500 thereby unlocking the base 400 and initiating the first stage of operation. The first spring 320 releases its energy and propels the base 400 in the distal direction thereby causing the combined inner tube 120/outer cannula 130 to be driven (fired) into the target tissue. This movement is shown in FIG. 2.

As described herein, the second stage automatically follows the first stage and the forward projection of the curvilinear tube 150 along the top surface 406 causes the rotation of the inner tube 120 relative to the outer cannula 130, thereby causing the winding up (activation) of the snare. This results in the tissue specimen at the target site being captured. The device 100 can then be removed from the patient's body and then the first and second reset mechanisms can be actuated to cause the resetting of the curvilinear tube 150 which results in the snare opening to allow the user to retrieve the captured specimen. FIG. 3 shows the device 100 after completion of the first and second stages.

Figure 4:
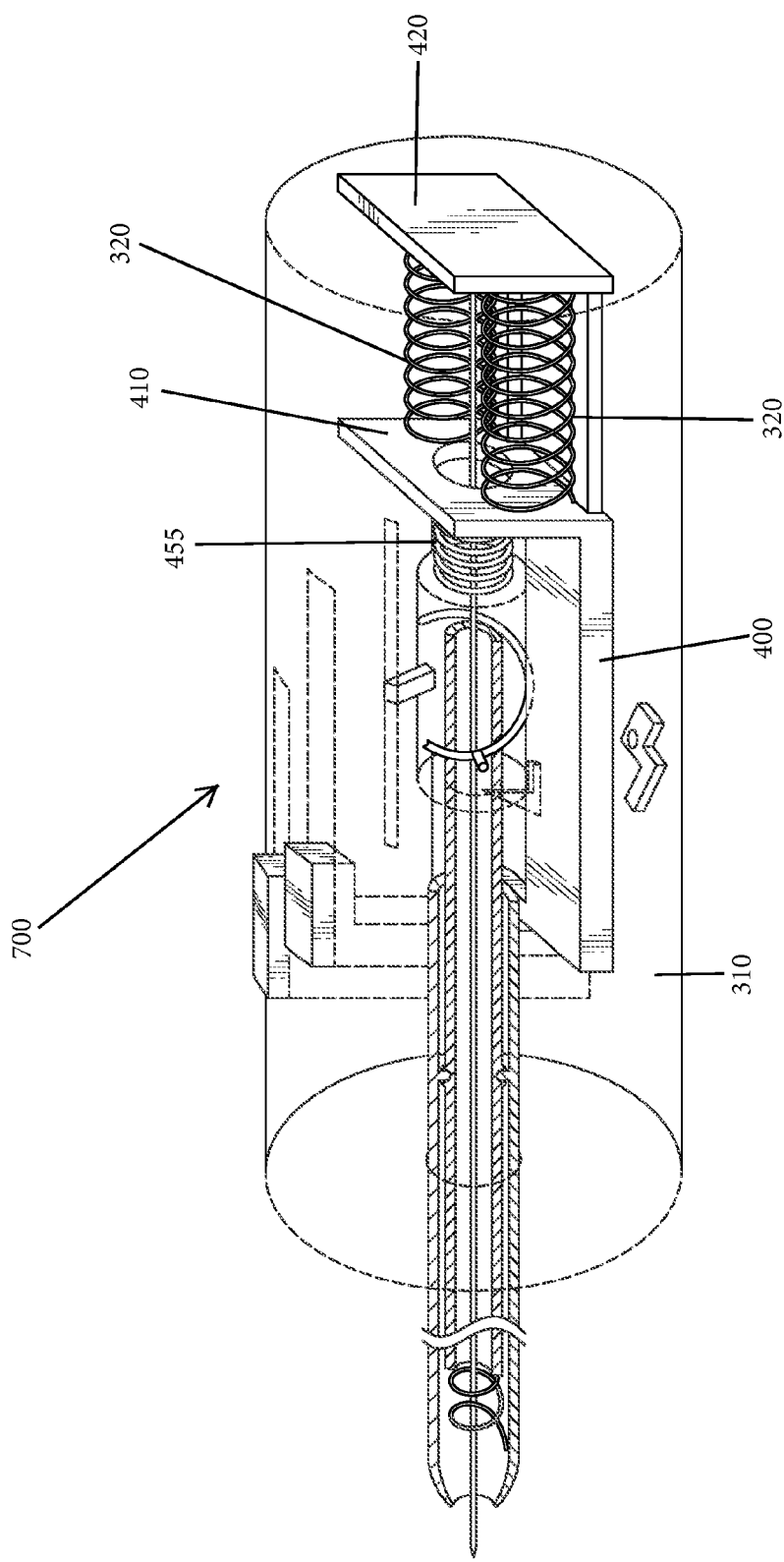
FIG. 4 is a side perspective view of a biopsy device according to a second embodiment.
Figure 5:
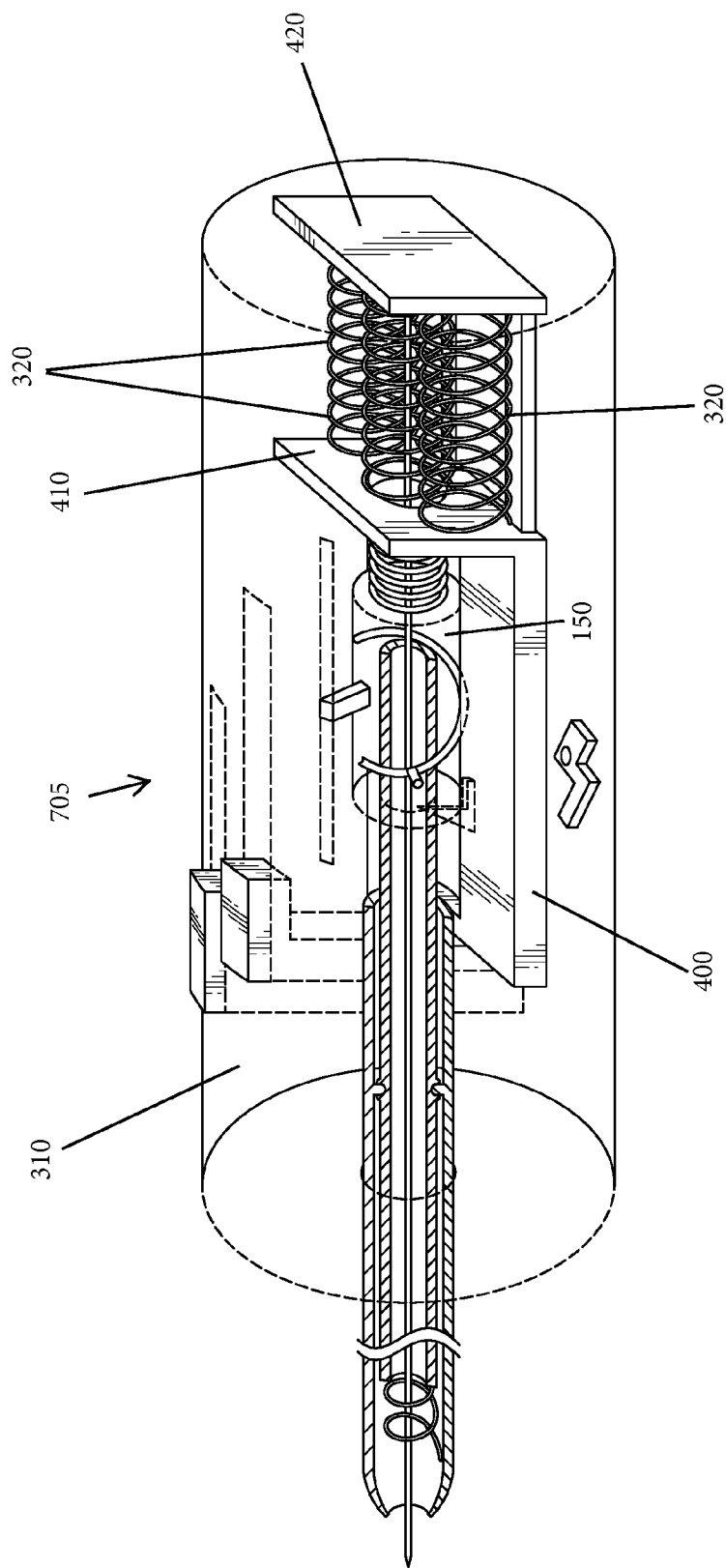
FIG. 5 is a side perspective view of a biopsy device according to a third embodiment.

FIG. 4 shows a device 700 that is similar to the device 100 with the exception that the device 700 includes two first springs 320. The two springs 320 are disposed side-by-side with the two springs 320 being disposed outside (lateral) to the opening 413 formed in the wall 410. The use of two springs 320 provides increased biasing force to drive the inner tube/outer cannula into the target tissue. FIG. 5 shows a device 705 with an additional first spring 320 and therefore, there are three total first springs to create the biasing force and propel the base 400 in the distal direction. The center spring 320 can be disposed around the opening 413 in the wall 410. As can be appreciated any number of multiple springs can be positioned between the 410 and 420 walls.

FIG. 6 shows a different reset mechanism 710 and in particular, the reset mechanism 710 includes a double pronged single slider 715. The slider 715 slidably travels within a pair of linear guide slots 720 formed in base 400. The slider 715 includes a first section 717 that is accessible to the user along the outside of the handle body 310. The first section 717 can be a ribbed pusher which is contacted by the user's thumb. The slider 715 has first and second prongs 718, 719 that depend downwardly from the first section 717. However 718 and 719 could also represent the two sides of a curvilinear double pronged member, or other similar configurations. The base 40 includes a pair of guide slots 720 for receiving the two respective prongs 718, 719. The two slots 720 are open at the distal end of the base 400 and open into the concave surface at 722 and terminate at proximal ends 724. The slots 720 can pass all the way through the base 400 or can be recessed in the base 400 but not pass all the way therethrough. The slots 720 can terminate at ends 724 that are within the concave surface 407 allowing the prongs to be displaced proximally into the concave recess.

The slider 715 operates by being directed into the open ends of the slots 720 and as the slider 715 is directed in the proximal direction, the two prongs 718, 719 contact the distal end of the curvilinear tube 150 and continued driving of the slider 715 causes the curvilinear tube 150 to rest to the initial position. Once the curvilinear tube 150 is displaced proximally, continued driving of the slider 715 results in the prongs 718, 719 contacting the closed ends 724 and thus, continued driving of the slider 715 causes the entire base 400 to move in the proximal direction. Once the base 400 resets to the initial position, the slider 715 can then be moved in the distal direction.

FIGS. 7 and 8 show another variation of the slider 715 in that the prongs 718, 719 are disposed above the upper surface 406 of the base 400 but are spaced and positioned such that the prongs 718, 719 contact the distal end of the curvilinear tube 150. The driving of the slider 715 in the proximal direction results in the prongs 718, 719 passing over the upper surface 406 and then into contact with the curvilinear tube 150. Continued driving of the slider 715 causes movement of the curvilinear tube 150 in the proximal direction until it is reset. The proximal end of the concave section 407 can include a stop (such as a tab or lip) and therefore, when the curvilinear tube 150 is driven into contact with this stop, the continued driving of the slider 715 in the proximal direction causes the resetting of the base 400 since the stop is part of the base 400 and driving of the tube 150 against the stop causes a driving of the base 400 in the proximal direction.

FIG. 8 shows the slider 715 in a first position spaced from the base 400 and curvilinear tube 150 and FIG. 7 shows a second position, in which the slider 715 is in contact with the curvilinear tube 150. As shown in FIGS. 7 and 8, the length of the concave section 407 can be customized.

Figure 9:
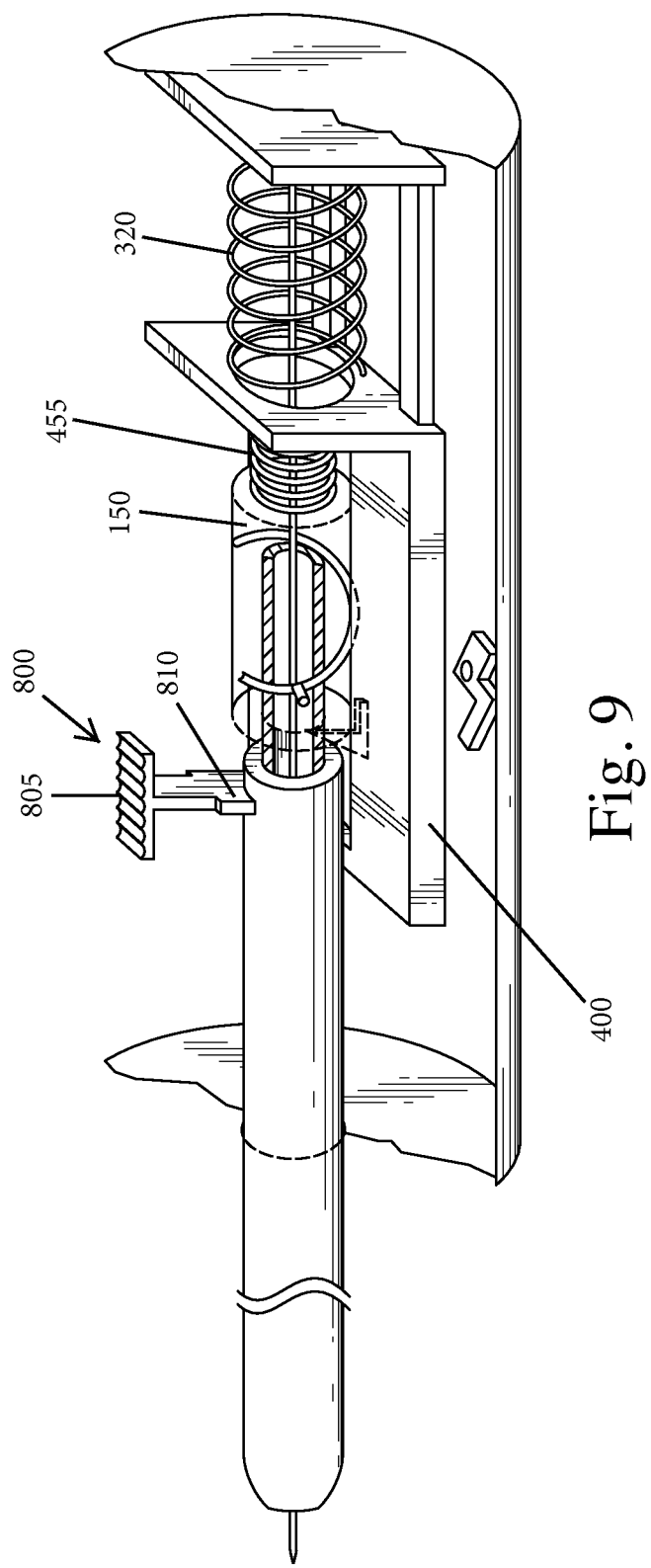
FIG. 9 is a side perspective view of a reset mechanism according to another embodiment in a first position.

FIG. 9 shows a different reset mechanism 800 in the form of a single pronged single slider. The configuration is similar to the mechanism shown in FIG. 1 except for the fact that instead of including two sliders to sequentially reposition the curvilinear tube 150 and then the base 400, one slider 805 is used. The slider 805 has one projecting element or prong 810. Unlike the previous embodiment, the prong 810 does not move within a track within the base 400 since it is positioned superior to the outer cannula 130. The prong 810 first engages the superior portion of the curvilinear tube 150. After repositioning the curvilinear tube 150 which then is locked into place by the re-engagement of the releasing lever (which is positioned inferior to the tube), continuing to apply force to the curvilinear tube 150 transmits the translational force to the base 400 which is then rebiased into its fireable position.

In order that a substantial force is not applied to the releasing lever during the re-biasing of the base 400, the curvilinear tube 150 can come to rest against a type of ledge in the base 400 which keeps it from translating beyond a certain position on the sled 400 when it is in its rebiased position.

What is claimed is:

1. A biopsy needle for collecting a tissue specimen comprising:
   a handle housing;
   an outer cannula that is at least partially received within the handle housing;
   an inner tube received within the outer cannula and configured to receive a stylet, wherein the outer cannula and inner tube extend distally beyond a distal end of the handle housing;
   a snare coil attached between the inner tube and the outer cannula;
   a movable base disposed within the handle housing, wherein the outer cannula is fixedly coupled to the base, the movable base being axially movable within the handle housing;
   an inner driven structure that is coupled to the inner tube and is configured to travel axially across an upper surface of the movable base, wherein the coupling between the inner driven structure and the inner tube is such that the axial driving of the inner driven structure imparts rotation to the inner tube relative to the outer cannula;
   a first biasing mechanism coupled to the movable base for driving the movable base in a distal direction when the first biasing mechanism releases its stored energy;
   a second biasing mechanism coupled to the inner driven structure for driving the inner driven structure in a distal direction when the second biasing mechanism releases its stored energy;
   wherein the first biasing mechanism defines a first stage of operation and the second biasing mechanism defines a second stage of operation, wherein in the first stage, the release of the stored energy of the first biasing mechanism causes the movable base and the inner tube and the outer cannula to travel axially in the distal direction and the second biasing mechanism is configured such that after the movable base travels a prescribed distance, the second biasing mechanism releases its stored energy to cause rotation of the inner tube relative to the outer cannula, thereby causing activation of the snare coil.

2. The needle of claim 1, wherein the outer cannula is fixedly attached to the upper surface of the base.

3. The needle of claim 1, wherein a proximal end of the inner tube is disposed within an interior of the inner driven structure.

4. The needle of claim 1, wherein the snare coil comprises a distal section of the inner tube with a distal end of the snare coil being attached to the outer cannula.

5. The needle of claim 1, wherein the inner driven structure comprises a curvilinear tube that has at least one helical shaped groove formed therein, the inner tube having at least one protrusion extending outwardly from an outer surface thereof and being received within the at least one helical shaped groove.

6. The needle of claim 5, wherein the helical shaped groove passes completely through a side wall of the curvilinear tube.

7. The needle of claim 5, wherein the inner tube includes a pair of protrusions disposed opposite one another and the curvilinear tube has two helical shaped grooves that are symmetrically opposite one another.

8. The needle of claim 5, wherein the curvilinear tube mates with a first guide that only allows the curvilinear tube to travel in the axial direction and prevents rotation of the curvilinear tube.

9. The needle of claim 8, wherein the curvilinear tube has a pin that is received within a linear slot that comprises the first guide.

10. The needle of claim 9, wherein the linear slot is formed in the handle housing.

11. The needle of claim 9, wherein the linear slot is formed in the upper surface of the base.

12. The needle of claim 5, wherein the upper surface of the base includes a concave recessed section in which the curvilinear tube rests and travels in an axial direction therein, the base including a first end wall at a proximal end wall of the base, wherein the curvilinear tube is disposed adjacent the first end wall.

13. The needle of claim 12, wherein the second biasing mechanism comprises a second spring that is in contact with a distal face of the first end wall and the first biasing mechanism comprises a first spring that is contact with a proximal face of the first end wall.

14. The needle of claim 13, wherein the base rides along a pair of guide rails disposed within the handle housing, the guide rails passing through a pair of longitudinal bores formed through the base.

15. The needle of claim 1, further including a first actuator that is configured to initiate the first stage and comprises a first structure that selectively contacts the base so as to lock the base in an initial locked position and is movable to a second position in which the first structure is removed from the base and the base is free to move and be driven axially as the first biasing mechanism releases its stored energy.

16. The needle of claim 15, further including a second actuator that is configured to initiate the second stage and comprises a second structure that selectively contacts the inner driven member so as to lock the inner driven member in an initial locked position and is movable to a second position in which the second structure is removed from the inner driven member and the inner driven member is free to move and be driven axially as the second biasing mechanism releases its stored energy.

17. A biopsy needle for collecting a tissue specimen comprising:
a handle housing;
an outer cannula that is at least partially received within the handle housing;
an inner tube received within the outer cannula and configured to receive a stylet, wherein the outer cannula and inner tube extend distally beyond a distal end of the handle housing;
a snare coil attached between the inner tube and the outer cannula;
a movable sled disposed within the handle housing, wherein the outer cannula is fixedly coupled to the movable sled, the movable sled being axially movable within the handle housing along one or more guides;
an inner driven structure that is coupled to the inner tube and is configured to travel axially a defined distance within a track formed in the movable sled while at the same being prevented from rotating during axial travel, wherein one of the inner tube and the inner driven structure includes a pin and the other of the inner tube and the inner driven structure includes a groove that receives the pin such that the axial driving of the inner driven structure imparts rotation to the inner tube relative to the outer cannula;
a first biasing mechanism coupled to the movable sled for driving the movable sled in a distal axial direction when the first biasing mechanism releases its stored energy;
a second biasing mechanism coupled to the inner driven structure for driving the inner driven structure in the distal axial direction along the movable sled when the second biasing mechanism releases its stored energy;
wherein the first biasing mechanism defines a first stage of operation and the second biasing mechanism defines a second stage of operation, wherein in the first stage, the release of the stored energy of the first biasing mechanism causes the movable sled and the inner tube and the outer cannula to travel axially in the distal direction for a defined distance and the second biasing mechanism is configured such that after the movable sled travels a prescribed distance, the second biasing mechanism is automatically tripped and releases its stored energy to cause the axial driving of the inner driven structure resulting in rotation of the inner tube relative to the outer cannula, thereby causing activation of the snare coil.

18. The needle of claim 17, further including a first manual reset mechanism that is accessible along an exterior of the handle housing for manually driving the inner driven structure in a proximal direction to cause the second biasing mechanism to store energy and to releasably lock the inner driven structure in an initial position, and a second manual reset mechanism that is accessible along an exterior of the handle housing for manually driving the movable sled in a proximal direction to cause the first biasing mechanism to store energy and to releasably lock the movable sled in an initial position.

19. The needle of claim 17, wherein the movable sled includes a proximal end wall and the first biasing mechanism is disposed between the proximal end wall and a proximal surface defined within the handle housing.

20. The needle of claim 17, further including a first release member that releasably engages the movable sled and is movable between an engaged position in which the movable sled is engaged and prevented from moving axially and a released position in which the movable sled can move in an axial direction and a second release member that releasably engages the inner driven structure and is movable between an engaged position in which the inner driven structure is engaged and prevented from moving axially and a released position in which the inner driven structure can move in an axial direction, wherein the movable sled includes a longitudinal slot to allow for passage of the second release member so as to permit the second release member to engage the inner driven structure.

* * * * *